United States Patent [19]

Byrne, Jr.

[11] Patent Number: 5,021,057
[45] Date of Patent: Jun. 4, 1991

[54] CORNEAL EXPULSIVE HEMORRHAGE INSTRUMENT

[75] Inventor: James B. Byrne, Jr., Huntsville, Ala.

[73] Assignee: Vitreoretinal Development, Inc., Birmingham, Ala.

[21] Appl. No.: 544,990

[22] Filed: Jun. 28, 1990

[51] Int. Cl.⁵ .................... A61F 9/00; A61B 17/00
[52] U.S. Cl. ................... 606/107; 606/201; 623/4
[58] Field of Search ............. 606/107, 166, 201; 128/163, 858; 604/294, 297, 298, 300; 623/4–6

[56] References Cited

U.S. PATENT DOCUMENTS

| | | | |
|---|---|---|---|
| 4,406,285 | 9/1983 | Villasenor et al. | 606/166 |
| 4,572,182 | 2/1986 | Royse | 606/201 |
| 4,990,150 | 2/1991 | Tsubota et al. | 606/107 |

Primary Examiner—Ronald Frinks
Attorney, Agent, or Firm—Jennings, Carter, Thompson & Veal

[57] ABSTRACT

An instrument to be used during ocular surgery for the rapid closure of anterior segment openings and the control of expulsive choroidal hemorrhage and the resulting damage caused by this complication. The instrument is to be positioned over the anterior ocular surface of the eye at the first indication of hemorrhage or "posterior pressure". One or more dimples located on the upper surface of the instrument allows the insertion of a elongated member for holding the instrument in place while maintaining the intraocular pressure. An opening is also present which allows a surgeon to insert sutures into the underlying eye while the instrument is in place and also aids in the movement of the instrument about the anterior ocular surface of the eye by insertion of a probe or forceps. The instrument is transparent, allowing the surgeon to visually monitor the intraocular events.

21 Claims, 3 Drawing Sheets

FIG. 1
FIG. 6
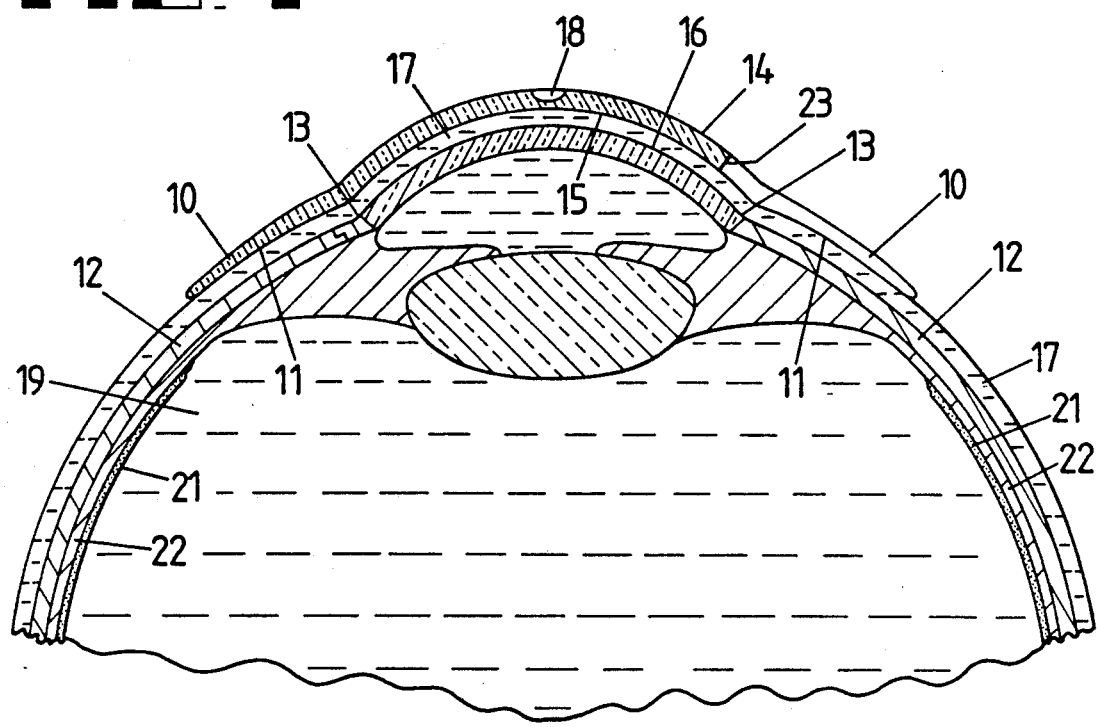
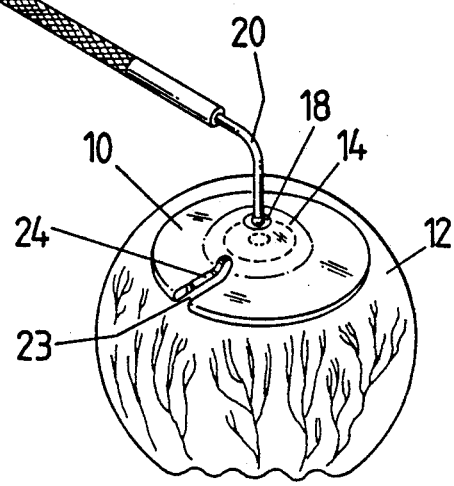

CORNEAL EXPULSIVE HEMORRHAGE INSTRUMENT

FIELD OF THE INVENTION

The present invention relates to an instrument to be used in eye surgery. More particularly, the present invention relates to an instrument to be used in surgery in the anterior segment of the eye, including cataract and corneal transplant surgery, which when placed over the anterior ocular surface will aid in closing the surgical incision in an open globe, maintaining a positive intraocular pressure, and preventing the expulsion of intraocular structures due to hemorrhage or choroidal detachment.

BACKGROUND OF THE INVENTION

Expulsive choroidal hemorrhage is one of the most devastating complications that can occur during intraocular surgery. Permanent and frequently total vision loss in the involved eye is the common result. Damage occurs when leakage from a choroidal blood vessel elevates the uvea off its scleral bed resulting in the expulsion of intraocular tissues, including the retina through the surgical incision. The hemorrhage or fluid leakage is thought to result from a change in the transvascular pressure gradient due to the globe being surgically opened and depressurized. This complication occurs at a rate of approximately 1 in 10,000 cataract operations and 1 in 1,000 penetrating kepatoplasties, resulting in the loss of approximately 200 eyes per year in the United States.

The only known methods for controlling a choroidal hemorrhage are to reseal the eyeball or emergency surgical drainage of suprachoroidal hemorrhage. Closing the surgical incision prevents the expulsion of ocular contents and allows the intraocular pressure to rise to a level such that further bleeding is stopped. Surgical closure of a cataract incision or penetrating keratoplasty opening with sutures takes at least several minutes and frequently cannot be accomplished before important intraocular structures have been extruded through the wound. At this time, the suggested method for rapidly closing the globe is the placement of the surgeon's gloved finger over the cornea or graft opening and the application of pressure until the bleeding stops.

Several disadvantages of this method are evident. Sealing the wound with a finger may be difficult or impossible. Excessive pressure in the absence of an adequate seal may itself cause expulsion of intraocular contents. Excessive elevation of intraocular pressure due to digital compression above that required to seal the wound may cause permanent damage due to interruption of ocular blood flow. A good deal of guesswork is involved in determining whether the bleeding has stopped and when it is safe to remove the finger. Releasing the pressure can stimulate further bleeding and allow intraocular tissues to prolapse through the wound. If the bleeding has not stopped at the time the finger is removed, the finger must be reinserted and more pressure applied, thereby increasing the chance of additional damage to the cornea.

Pressure on the anterior corneal surface by the surgeon's finger everts the cornea and presses its delicate inner lining (endothelium) against the iris, lens and intraocular tissues. The thin layer of cells lining the cornea are responsible for keeping the cornea clear. These cells are extremely susceptible to damage and are irreplaceable. The distortion of the cornea and contact with other structures required to control an expulsive hemorrhage usually causes sufficient damage to cause permanent clouding of the cornea. If the eye is salvaged, corneal transplant surgery is usually required to restore a clear front surface to the eye.

Another disadvantage of using digital pressure to seal the anterior segment is that the surgeon's finger obstructs the view into the eye. This makes it difficult or impossible to monitor the progress of the hemorrhage.

Because of visualization problems and distortion of the normal anatomical position of the wound margins, it is not possible to suture the wound while digital pressure is maintained. When the surgeon's finger is removed, either to look into the eye or to attempt suturing, the pressure is decreased, stimulating further bleeding and allowing intraocular tissues to prolapse.

The iris, ciliary body, and retina are delicate intraocular tissues that if extruded from the eye are usually irreversibly damaged. If the retina is extruded from the eye, permanent blindness of that eye almost certainly results.

SUMMARY OF THE INVENTION

It is the principal object of the present invention to provide an inexpensive, readily available, reusable instrument to facilitate temporary closure of anterior segment surgical incisions, thereby preventing uveal extrusion and elevating the intraocular pressure to suppress further bleeding in the event of choroidal hemorrhage. This can be accomplished without causing permanent damage to cornea.

Yet another object of the present invention is to allow the insertion of sutures into the eye with the instrument in place while maintaining a sealed, pressurized globe. These sutures will provide permanent closure of the wound. These objectives are accomplished by this invention through the placement of a transparent, substantially rigid, dome-shaped covering which can be placed over the cornea and anterior sclera of the eye in order to effectively close an anterior segment opening and reseal the eye. Closure of the globe will prevent the expulsion of intraocular tissues and tamponade any bleeding within it. This covering is to be composed of a material that will allow sterilization so that it may be reused. The transparent construction of the device allows for an unobstructed view into the eye during the emergency and the ability to monitor the progress of the choroidal elevation during treatment.

During corneal transplantation surgery, a disc-shaped piece of the central cornea, "the corneal button", is removed from the host and replaced with a similar piece from a donor eye. The anterior segment of the eye is open in such a way that rapid replacement of the graft tissue is not possible. The present invention allows for rapid closure of an "open sky" corneal incision either with or without a "corneal button" in place.

Once the choroidal hemorrhage has been controlled, the present invention can be advanced eccentrically on the cornea in such a way as to allow one part of the graft/host interface to be sewn together. This can be accomplished while maintaining a closed seal of the anterior segment and pressurization of the eye.

The covering has two distinct regions: an outer region which circumscribes an inner region, both having a concave bottom surface whose curvature approximates the anterior surface of the human eye. When the instrument is placed on the eye a seal is formed between the instrument and the anterior ocular surface. The opposing tissue edges of a typical cataract incision are reapproximated in their normal anatomic position, functionally resealing the globe. This seal is maintained by a thin layer of fluid which separates the instrument from the surface of the eye. In "open sky" procedures, where corneal tissue is not present to be reapproximated, the device itself acts as a cap sealing the anterior corneal opening.

The upper surface contains one or more dimples into which a probe in the form of one or two elongated members may be inserted to assist in holding the instrument in place. Pressure applied to the upper surface of the instrument with the probe is transferred through the fluid and to the anterior ocular surface of the underlying eye. This pressure aids in holding the instrument in place, creating a seal between opposing edges of the surgical incision for the purpose of resealing the eye, preventing uveal expulsion, and tamponading intraocular hemorrhage. Reopposing the tissues in their normal anatomic position allows the eye to be resealed with a minimum of pressure, preventing damage to intraocular tissues and compromise of ocular blood flow which can result from excessive pressure. The cornea need not be everted or have its delicate inner lining pressed against intraocular contents. The likelihood of permanent corneal clouding is thereby reduced.

The covering also contains a radial opening extending from the outer annular region into the inner region that is of sufficient size to allow the insertion of sutures into the underlying tissues and the rotation of the instrument without removing the instrument from the ocular surface.

The application of this instrument early in the course of a choroidal detachment greatly decreases the chance of intraocular tissues being extruded from the eye and irreversibly damaged. At the first indication of a possible hemorrhage, the instrument may be applied. Because of its transparency, the surgeon is able to view into the eye allowing him to determine when the hemorrhaging has stopped. This invention gives the surgeon a way to rapidly control the hemorrhage without causing the excessive damage that was likely to result from digital pressure, which is the currently recommended method of controlling such hemorrhages. Another advantage is that the surgeon may also insert sutures, permanently sealing the eye, while the instrument remains in place and the eye remains sealed. Another advantage is that the cornea is not distorted from its normally convex slope and its delicate inner lining is not damaged by contact with intraocular contents. This may prevent permanent corneal clouding which is the typical result of sustained digital pressure on the corneal surface. Overall, the use of this instrument provides a safer and more practical way of rapidly closing an open eye and controlling expulsive choroidal hemorrhage.

BRIEF DESCRIPTION OF THE DRAWINGS

Instrument embodying features of my invention are illustrated in the appended drawings which form a portion of this disclosed and wherein:

FIG. 1 is a cross sectional view showing the instrument on the anterior ocular surface of the eye;

FIG. 6 is a perspective view showing the probe on the anterior ocular surface of the eye as it will appear during surgery;

DESCRIPTION OF A PREFERRED EMBODIMENT

Figure 2:
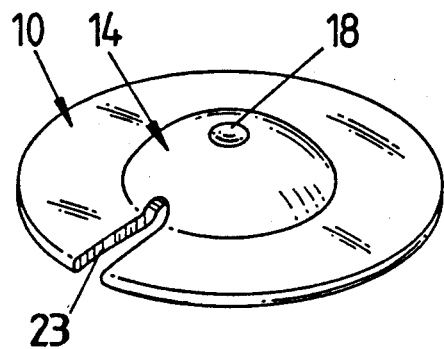
FIG. 2 is a perspective view of the upper surface of the instrument.
Figure 3:
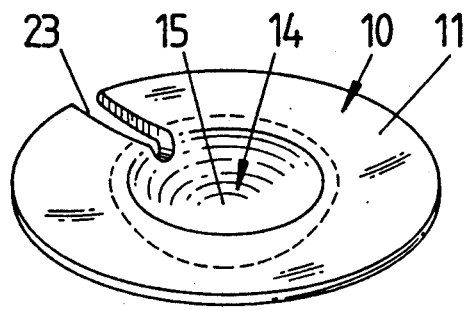
FIG. 3 is a perspective view of the bottom surface of the instrument.

Referring to the drawings for a clearer understanding of the invention, it should be noted that the present invention's contemplated use is for the purpose of rapidly closing and eye opened in the anterior segment and controlling expulsive choroidal hemorrhage. This instrument is in the shape of a dome made of a durable, sufficiently rigid, reusable, transparent material that resists deformation by intraocular pressure while allowing a satisfactory degree of flexibility to aid comformity with the anterior ocular surface of the eye without causing damage thereto. As shown in FIGS. 1-3, this dome includes an outer annular region 10 whose concave bottom curvature 11 approximates that of the anterior sclera 12 and adjoining limbus 13 and an inner region 14 whose concave bottom surface 15 approximates that of the cornea 16 of the eye.

As further indicated by FIG. 1, the dimensions of the inner region 14 should be of sufficient size to allow coverage of the cornea 16 with the outer annular region 10 extending a sufficient area over the sclera 12 to aid in the maintenance of a seal created by urging the opposing sides of the surgical incision into place. The central dome should be able to seal a central corneal opening as commonly created in corneal transplant surgery. A thin layer of fluid 17 supplied by irrigation during surgery exists between the instrument and the surface of the eye as illustrated, and acts as a cushion between the two. This layer of fluid 17 aids in controlling the rotation of the instrument about the surface of the eye for the insertion of sutures and in maintaining the seal between the surgically severed portions, which as shown in FIG. 1, are typically a stepped incision such that the tissue is easily reapproximated and forms a seal upon the application of external pressure.

Figure 7:
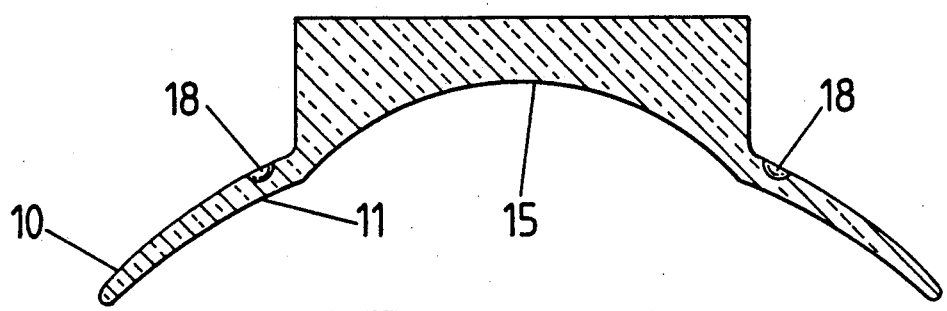
FIG. 7 is a sectional view of the instrument showing one alternative of the upper surface of the instrument which has a flat upper exterior with a concave inner annular interior with more than one dimple located outside the inner annular region allowing for clear visibility of the eye.
Figure 8:
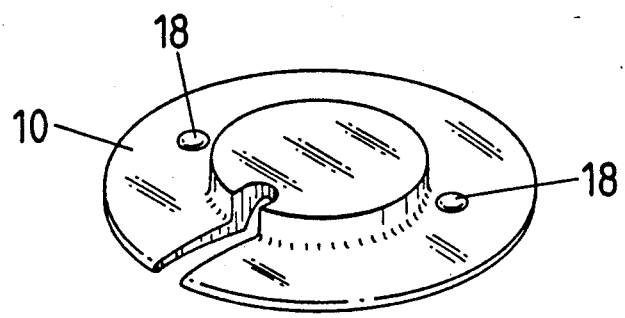
FIG. 8 is a perspective view of the instrument showing one alternative of the upper surface of the instrument which has a flat upper exterior with a concave inner annular interior with more than one dimple located outside the inner annular region allowing for clear visibility of the eye.

One dimple 18 located in substantially the middle upper surface of the inner region 14 as shown in FIGS. 2 and 6, or two dimples located on the upper surface of the outer region as shown in FIGS. 7 and 8. After the possibility of hemorrhage is found to exist, a probe 20, in the shape of a slender elongated member or forceps, may be inserted into the dimple(s) 18 to allow the position of the instrument to be maintained. The probe is also utilized to apply pressure to the instrument so that the intraocular pressure of the eye may be elevated to prevent the expulsion of the vitreous 19, retina 21 and choroid 22, and tamponade the bleeding.

Figure 4:
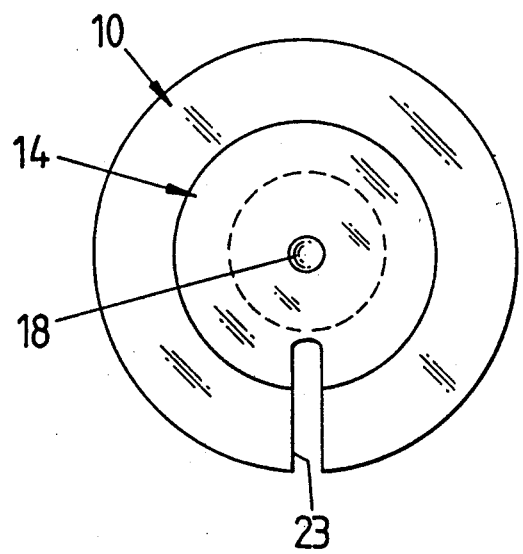
FIG. 4 is a top plan view of the upper surface of the instrument showing one alternative of the opening for suturing.
Figure 5:
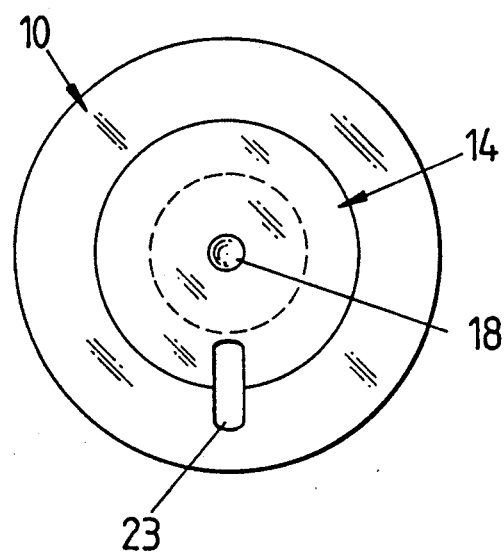
FIG. 5 is an additional top plan view of the upper surface of the instrument showing another alternative of the opening for suturing.
Figure 9:
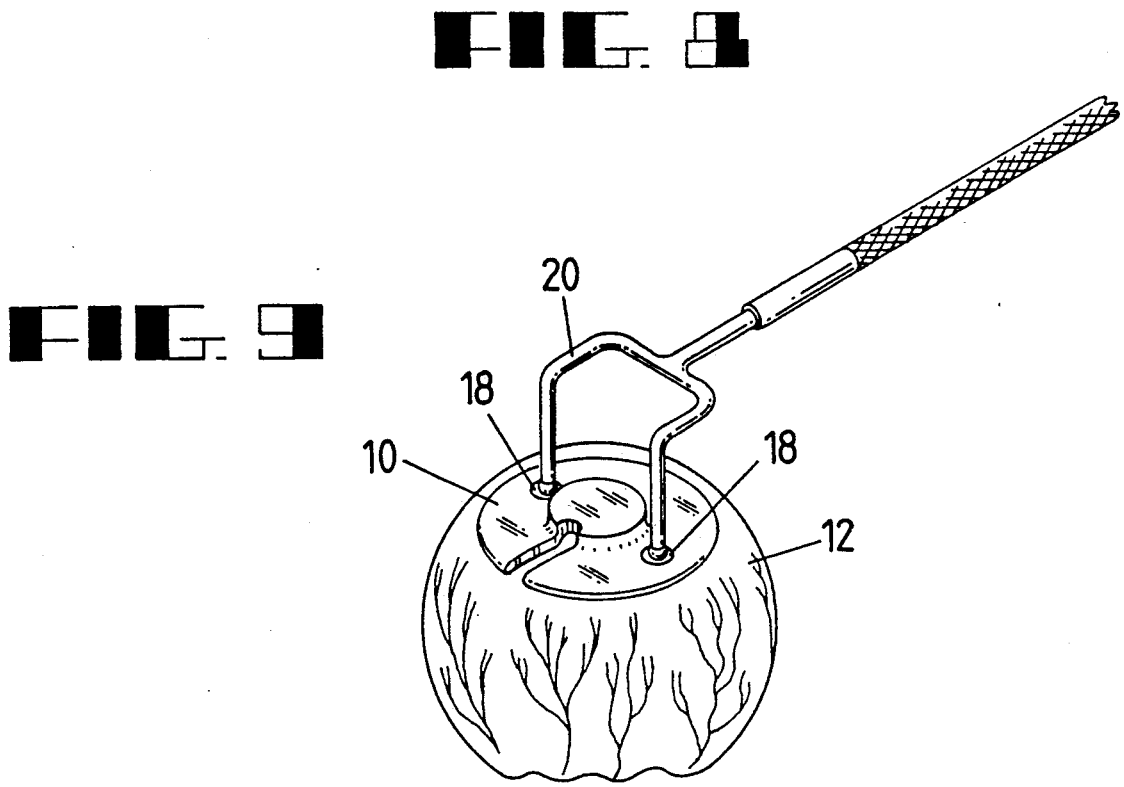
FIG. 9 is a perspective view showing an alternate probe engaged on the anterior ocular surface of the eye as it will appear during surgery utilizing more than one dimple.

The instrument also contains a single opening 23, as shown in FIGS. 4-5, which is of sufficient size to allow the insertion of sutures into the underlying eye while maintaining pressure on the eye and without removal of the instrument from the anterior ocular surface. This opening may be in the form of a radially formed opening which extends through the entire outer annular region 10 and into the inner region 14 as shown by FIG. 4. An alternate type of opening would be in the form of a window 23 as shown in FIG. 5 which is contained within the instrument and partially extends into both the outer annular region 10 and inner region 14 without completely crossing either. Once a suture is in place, the instrument may be rotated to the site of the next suture by gently pushing against the side 24 of the opening with forceps or a second elongated probe causing rotation of the instrument to occur about the axis created by the insertion of a probe into the dimple as illustrated by FIG. 6. The multiple dimpled instrument FIGS. 7 and 8 may be rotated by a two-pronged probe FIG. 9.

After the surgery is completed, the instrument may be removed from the surface of the eye, autoclaved and/or gas sterilized without causing the instrument to become opaque or distorted, and stored until needed again. From the foregoing, it should be clear that the present instrument and method represent a substantial improvement over the prior art.

An alternate embodiment utilizes an exterior inner region which is flattened and an interior inner region which is concave. Further, the alternate instrument illustrates the use of multiple dimples located in the outer flattened region. The alternate embodiment results in greater visibility of the eye enabling the surgeon to determine whether hemorrhaging has ceased.

While I have shown my invention in two forms, it will be obvious to those skilled in the art that it is not so limited but is susceptible of various changes and modifications without departing from the spirit thereof.

What I claim is:

1. An instrument for the control of ocular expulsive choroidal hemorrhage during intraocular surgery, comprising:
   (a) a substantially rigid, transparent dome having an outer annular region with a concave bottom surface whose curvature approximates the curvature of the sclera proximate the limbus of the eye;
   (b) an inner region circumscribed by said outer annular region having a concave bottom surface whose curvature approximates the curvature of the cornea of the eye; and
   (c) an aperture formed in said outer annular region and extending into said inner region to permit access to the underlying eye.

2. An instrument as defined in claim 1 wherein said instrument is constructed of a durable material that is sufficiently rigid to resist deformation by intraocular pressure while allowing a satisfactory degree of flexibility to aid conformity with the anterior ocular surface without causing damage thereto.

3. An instrument as defined in claim 1 wherein said instrument contains a single aperture.

4. An instrument as defined in claim 3 wherein said aperture occupies a minimal amount of surface area of said instrument so that a seal may be maintained while allowing the insertion of sutures into the underlying eye without the removal of said instrument from the eye.

5. An instrument as defined in claim 1 wherein said instrument further comprises a single dimple found substantially at the center of said dome and on the upper surface thereof and means engageable with said dimple for holding said instrument in place.

6. An instrument as defined in claim 5 whereby said means comprises an elongated member engageable in said dimple with the application of sufficient pressure to prevent further expulsion of ocular contents through an opening in the anterior surface of the eye.

7. An instrument as defined in claim 1 wherein said instrument comprises one or more dimples found substantially on either side of the inner region of the upper surface thereof and means engageable with said dimples for holding said instrument in place.

8. An instrument as defined in claim 7 whereby said means comprises an elongated member engageable in said dimples with the application of sufficient pressure to prevent further expulsion of ocular contents through an opening in the anterior surface of the eye.

9. An instrument as defined in claim 1 constructed of a material that may be reusable by autoclaving and/or gas sterilization without causing said instrument to become opaque or distorted.

10. An instrument as defined in claim 1 that is of sufficient dimensions in relation to the average eye as to allow coverage of the cornea, limbus and a sufficient area of the sclera so that a seal may be formed by urging the previously surgically severed portion of the sclera into the mating abutment.

11. An instrument as defined in claim 1 that is of sufficient dimensions in relation to the average eye as to allow coverage of the cornea, limbus, and a sufficient area of the sclera so that an anterior corneal opening, created during penetrating keratoplasty surgery, can be sealed by placing it's dome-shaped undersurface over said anterior corneal opening.

12. An instrument for preventing ocular expulsive choroidal hemorrhage during eye surgery comprising:
   (a) a covering whose bottom surface is adapted to the curvature of the anterior ocular surface of the eye in order to form a seal by urging the opposing edges of a surgical incision in the eye into abutment or covering a central corneal opening including;
   (b) an outer band having a concave bottom surface conforming to the curvature of a human sclera and limbus;
   (c) an inner region whose concave bottom surface conforms with the curvature of a corneal button;
   (d) a slot formed in said covering extending through the outer band and the inner region;
   (e) at least one dimple located on an upper surface of said covering; and
   (f) a central region adapted to provide a view into the eye.

13. An instrument as defined in claim 12 wherein said instrument is made of a transparent, substantially rigid material.

14. An instrument as defined in claim 12 wherein said slot extends from the outer perimeter of the instrument into the inner region which is of sufficient size to allow manipulation of the underlying region of the eye for the placement of sutures.

15. An instrument as defined in claim 12 further comprising an elongated member selectively insertable into said dimple for controlling movement of said instrument.

16. An instrument as defined in claim 12 wherein said instrument is composed of material which allows for its reuse following sterilization.

17. An instrument as defined in claim 12 wherein the dimensions of the concave bottom of said inner region are to be determined by the curvature of the cornea, the dimensions of the concave bottom of said outer band are to be determined by the curvature of the sclera and which outer band extends a sufficient distance over the sclera to allow the movement and placement of sutures in previous surgical incisions in the underlying eye.

18. A method for using a covering including a substantially rigid, transparent dome having an outer annular region with a concave bottom surface whose curvature approximates the curvature of the sclera and proximate limbus of the eye, an inner region circumscribed by said outer region having a concave bottom surface whose curvature approximates the curvature of the corneal button of the eye with one or more dimples on the upper surface and an aperture formed through said outer annular region and extending into said inner region to permit access to the underlying eye for the purpose of closing an anterior segment opening in the eye and the control of ocular expulsive chorioidal hemorrhage during intraocular surgery and the like, comprising:

(a) placement of said dome over the anterior ocular surface after incisions have been made and the possibility of expulsive chorioidal hemorrhage is found to exist;

(b) creating a seal between the sclera and/or cornea where the said outer annular region and the said inner region come in contact with the anterior ocular surface;

(c) holding said dome in place over the eye by the use of one or more elongated member inserted into said one or more dimples; and (d) using an elongated tool to move said dome around the anterior ocular surface.

19. A method as defined in claim 18 wherein said dome is placed over said anterior ocular surface of the eye in such a way that contact of the outer annular region and the inner region of said dome conforms with the cornea, sclera, and limbus of the eye to maintain the eye in its substantially normal shape.

20. A method as defined in claim 18 further comprising applying pressure to said elongated members when inserted into said dimple will allow sufficient pressure to be exerted upon said covering so that the intraocular pressure of the eye may be maintained while also effectuating the seal between the previously surgically severed edge of the sclera and/or cornea to prevent further expulsion as well as maintaining the position of said instrument.

21. A method as described in claim 18 whereby a second elongated probe or forcep is utilized to rotate said covering about an axis such that sutures may be sewn into the eye beneath said instrument without removing the instrument from said oculur surface.

* * * * *